United States Patent [19]
Hill

[11] Patent Number: 5,279,837
[45] Date of Patent: Jan. 18, 1994

[54] STYPTIC COMPOSITION

[76] Inventor: Richard J. Hill, 220 Locust, Apt. 26F, Philadelphia, Pa. 19106

[21] Appl. No.: 492,291

[22] Filed: Feb. 28, 1990

Related U.S. Application Data

[63] Continuation of Ser. No. 258,039, Oct. 14, 1988, abandoned.

[51] Int. Cl.⁵ .................... A61K 33/06; A61K 33/04
[52] U.S. Cl. .................................... 424/682; 424/709
[58] Field of Search ........................................ 424/682

[56] References Cited

U.S. PATENT DOCUMENTS

| | | | |
|---|---|---|---|
| 4,331,653 | 5/1982 | Brown et al. | 514/502 |
| 4,395,398 | 7/1983 | Yamamoto | 424/147 |
| 4,748,022 | 5/1988 | Busciglio | 514/716 |
| 4,867,967 | 9/1989 | Crutcher | 424/78.05 |

*Primary Examiner*—Zohreh A. Fay
*Attorney, Agent, or Firm*—Connolly & Hutz

[57] ABSTRACT

A styptic composition, in the form of a stable cream, for stopping bleeding from cuts received during shaving. The composition comprises aluminum sulfate, aloe, a humectant and water. The composition may optionally include a coloring agent, a fragrance, an anesthetic, or a preservative.

2 Claims, No Drawings

STYPTIC COMPOSITION

This application is a continuation, of application Ser. No. 258,039, filed Oct. 14, 1988 now abandoned.

FIELD OF THE INVENTION

The invention relates to an improved styptic composition, in the form of a stable cream, for use primarily in connection with shaving to rapidly and effectively curtail bleeding from minor nicks and cuts.

BACKGROUND OF THE INVENTION

Nicks and cuts on the chin, lips, face and other areas are a virtually inevitable consequence of regular blade shaving. Nicks and cuts can also be a significant problem for women when shaving their legs or underarms. Shaving cuts, especially in the area of the face or around the lips, tend to bleed profusely, and it can be quite difficult to halt the flow of blood.

Aluminum sulfate is a commonly employed styptic agent which is used to stop bleeding from shaving cuts. Solid sticks are available which consist essentially of about 90% aluminum sulfate and 10% of an inert filler. While it is desirable to apply a high concentration of aluminum sulfate directly to a cut in order to stop bleeding, the solid stick form of aluminum sulfate has certain disadvantages. A styptic stick can often be uncomfortable to use. The stick must be wetted before each use, and when the stick is stored between uses, the stick can harden, stick to its container, and become difficult to rewet and reuse. Moreover, rubbing of the stick on the cut can also result in scarring or redness of the area where the stick is applied.

U.S. Pat. Nos. 4,166,108 and 4,331,653 to Brown disclosed styptic lotions or creams containing a metal salt such as aluminum sulfate. The compositions are designed to be applied to major, open wounds without fear of inducing shock. The disclosed compositions contain 25% or less by weight of the metal salt. The disclosed compositions would not be completely satisfactory for application to shaving cuts. Due to the low content of metal salt, the composition would not act to halt bleeding from a small cut substantially immediately, and would have to be reapplied repeatedly, thereby permitting a scab to form over the area of the cut.

A liquid styptic composition, which is believed to be currently available, consists of a metal salt provided in an alcohol carrier. The liquid formulation tends to run down a user's face when it is applied, and several repeated applications of the composition are often necessary to stop bleeding from a small cut.

A need exists for a fast acting styptic composition which substantially immediately curtails bleeding from a small cut upon application, yet avoids the disadvantages associated with use of a solid styptic.

SUMMARY OF THE INVENTION

The invention comprises a styptic composition in the form of a stable cream. The cream form of the composition permits direct application of the composition to small cuts without running or dripping. The composition contains about 50-80% by weight of aluminum sulfate as the active ingredient. Due to the high concentration of aluminum sulfate, the composition acts to curtail minor bleeding substantially immediately upon application. The composition contains aloe, which imparts to the formulation a cream form, and a humectant, which stabilizes the cream and prevents loss of moisture during storage. The composition may also optionally contain one or more of a coloring agent, a fragrance, an anesthetic and a preservative.

DETAILED DESCRIPTION OF THE INVENTION

The composition of the invention provides a composition for quickly and effectively curtailing the flow of blood from a small cut. The composition is provided in cream form, which is substantially nonrunning and substantially remains in the area to which it is applied.

The active ingredient of the composition is aluminum sulfate, which is the most efficient metal salt known for stopping bleeding. Aluminum sulfate is available commercially in the form of a powder. By using aluminum sulfate in a relatively high concentration in the composition, it is possible to substantially immediately curtail bleeding from a small cut upon application of the composition to the cut. Aluminum sulfate is provided in the composition in an amount which is high enough to stop bleeding substantially immediately, yet low enough that the composition is capable of retaining the form of a flowable cream. The effective amount of aluminum sulfate which has been found to accomplish these different purposes is 50-80% by weight. A preferred range has been found to be between 60-75% by weight. Generally, in preparing the compositions of the invention, the aluminum sulfate is first combined with water to form a paste before adding the remaining constituents.

The composition is formed into a cream by the addition of aloe, preferably aloe vera. Aloe is included in an amount sufficient to form the composition into a flowable yet somewhat viscous cream. Aloe has an additional advantage in the formulation in that it acts as a mild natural anesthetic. Aloe also tends to render the formulation aesthetically pleasant to use. Generally, between about 2 and 20% by weight aloe in the formulation is effective.

A humectant is provided in the composition in an amount sufficient to render the cream stable and resistant to loss of moisture. Including a humectant also allows the composition to have a longer shelf life. Preferred humectants consist of polyhydric alcohols, such as glycerin.

A number of other constituents may optionally be included in the composition to impart various desirable characteristics to the finished composition. For example, an amount of an anesthetic, for example lidocaine, may be included to further reduce any stinging or burning sensation caused by the action of the aluminum sulfate. Generally, it is necessary to include the anesthetic in only a minor amount, for example, 2% or less by weight.

If desired, the composition may include a coloring agent or a fragrance, which serves to render the cream more aesthetically pleasing during use.

Also optionally, the composition may include a preservative, which enables large quantities of the composition to be prepared and stored with less risk of spoilage or contamination. Addition of a preservative also aids in extending the shelf life of the product. Suitable preservatives include BHA (butylated hydroxyanisol) or BHT (butylated hydroxytoluene).

To use the composition, a small amount, i.e., a dab of the composition, is applied directly to a bleeding cut or nick, using either the finger of any type of suitable applicator. Upon drying, the residual composition is easily washed off with water.

The following examples illustrate a formulation within the scope of the invention, and is provided as illustration and not as limitation.

EXAMPLE I

A styptic formulation was prepared having the following composition, given in percentages by weight:

| Component | Percent (w/w) |
|---|---|
| Aluminum Sulfate | 67% |
| Water | 20% |
| Aloe Vera | 5% |
| Glycerin | 5% |
| Lidocaine | 2% |
| BHA/BHT | 1% |

The formulation was prepared by combining the aluminum sulfate with water, followed by mixing to form a paste. The remaining constituents were added serially and mixed thoroughly. The formulation was stored at room temperature.

EXAMPLE II

The formulation of Example I was applied to a shaving nick inflicted during blade shaving by dabbing a small amount with the finger directly to the cut. The formulation was found to be very effective for substantially immediately curtailing bleeding from small shaving cuts, and did not produce significant pain when applied.

While a preferred form of the composition of the invention has been described above, minor variations will be apparent to those skilled in the art and are within the scope of the invention defined by the following claims.

I claim:

1. In a styptic composition for application to minor shaving cuts wherein the active ingredient is aluminum sulfate, the improvement comprising providing the composition in the form of a stable, flowable cream which can be applied to the minor cut without running or dripping, and which composition contains between 50 and 80% by weight aluminum sulfate to curtail minor bleeding substantially immediately upon application to the minor cut, the cream consisting essentially of aloe vera, a humectant, and containing an anesthetic.

2. The composition as claimed in claim 1, wherein the humectant is glycerin.

* * * * *